United States Patent
Henne et al.

(10) Patent No.: US 11,350,988 B2
(45) Date of Patent: Jun. 7, 2022

(54) BRONCHOSCOPIC MULTIMODALITY LUNG TUMOR TREATMENT

(71) Applicant: Uptake Medical Technology Inc., Seattle, WA (US)

(72) Inventors: Erik Henne, Seattle, WA (US); Robert Barry, Seattle, WA (US); Henky Wibowo, San Jose, CA (US)

(73) Assignee: Uptake Medical Technology Inc., Seattle, WA (US)

(*) Notice: Subject to any disclaimer, the term of this patent is extended or adjusted under 35 U.S.C. 154(b) by 376 days.

(21) Appl. No.: 16/108,118

(22) Filed: Aug. 22, 2018

(65) Prior Publication Data

US 2019/0076189 A1  Mar. 14, 2019

Related U.S. Application Data (60) Provisional application No. 62/556,785, filed on Sep. 11, 2017.

(51) Int. Cl.
| | | |
|---|---|---|
| *A61B 18/14* | (2006.01) | |
| *A61B 18/04* | (2006.01) | |
| *A61B 18/18* | (2006.01) | |
| *A61B 18/20* | (2006.01) | |

(Continued)

(52) U.S. Cl.
CPC .......... *A61B 18/1492* (2013.01); *A61B 18/04* (2013.01); *A61B 18/1815* (2013.01); *A61B 18/20* (2013.01); *A61B 2018/00017* (2013.01); *A61B 2018/00154* (2013.01); *A61B 2018/00541* (2013.01); *A61B 2018/00577* (2013.01); *A61B 2018/00994* (2013.01); *A61B 2018/048* (2013.01); *A61B 2090/374* (2016.02); *A61B 2090/376* (2016.02)

(58) Field of Classification Search
CPC ...... A61B 18/1492; A61B 2018/00994; A61B 2018/00541; A61B 2018/00017; A61B 18/04; A61B 2018/048; A61B 18/08

See application file for complete search history.

(56) References Cited

U.S. PATENT DOCUMENTS

| | | |
|---|---|---|
| 408,899 A | 8/1889 | Small |
| 1,719,750 A | 7/1929 | Bridge et al. |
| 3,507,283 A | 4/1970 | Thomas, Jr. |

(Continued)

FOREIGN PATENT DOCUMENTS

| | | |
|---|---|---|
| AU | 721086 B2 | 6/2000 |
| EP | 1003582 B1 | 2/2003 |

(Continued)

OTHER PUBLICATIONS

Becker, et al.; Lung volumes before and after lung volume reduction surgery; Am J Respir Crit Care Med; vol. 157; pp. 1593-1599; (1998) Oct. 28, 1997.

(Continued)

*Primary Examiner* — Linda C Dvorak
*Assistant Examiner* — Christine A Dedoulis
(74) *Attorney, Agent, or Firm* — Richard Batt (57) ABSTRACT

A minimally invasive medical technique for treating lung tumors includes use of multiple ablation modalities in a single procedure. Condensable vapor ablation and electrosurgical ablation are applied to treat the surface of the tumor and to debulk inner regions of the tumor, respectively.

17 Claims, 6 Drawing Sheets

(51) Int. Cl.
  *A61B 18/00* (2006.01)
  *A61B 90/00* (2016.01)

(56) References Cited

U.S. PATENT DOCUMENTS

| | | |
|---|---|---|
| 3,880,168 A | 4/1975 | Berman |
| 4,026,285 A | 5/1977 | Jackson |
| 4,713,060 A | 12/1987 | Riuli |
| 4,773,410 A | 9/1988 | Blackmer et al. |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,158,536 A | 10/1992 | Michael et al. |
| 5,263,951 A | 11/1993 | Spears et al. |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |
| 5,462,521 A | 10/1995 | Brucker et al. |
| 5,500,012 A | 3/1996 | Brucker et al. |
| 5,503,638 A | 4/1996 | Cooper et al. |
| 5,524,620 A | 6/1996 | Rosenschein |
| 5,529,076 A | 6/1996 | Schachar |
| 5,549,628 A | 8/1996 | Cooper et al. |
| 5,562,608 A | 10/1996 | Michael et al. |
| 5,575,803 A | 11/1996 | Cooper et al. |
| 5,591,157 A | 1/1997 | Hennings et al. |
| 5,620,440 A | 4/1997 | Heckele et al. |
| 5,695,507 A | 12/1997 | Auth et al. |
| 5,735,811 A | 4/1998 | Brisken |
| 5,752,965 A | 5/1998 | Francis et al. |
| 5,755,753 A | 5/1998 | Knowlton |
| 5,782,914 A | 7/1998 | Schankereli |
| 5,800,482 A | 9/1998 | Pomeranz et al. |
| 5,824,703 A | 10/1998 | Clark, Jr. |
| 5,827,268 A | 10/1998 | Laufer |
| 5,913,856 A | 6/1999 | Chia et al. |
| 5,957,919 A | 9/1999 | Laufer |
| 5,964,752 A | 10/1999 | Stone |
| 5,972,026 A | 10/1999 | Laufer et al. |
| 5,986,662 A | 11/1999 | Argiro et al. |
| 5,989,445 A | 11/1999 | Wise et al. |
| 6,032,077 A | 2/2000 | Pomeranz |
| 6,053,909 A | 4/2000 | Shadduck |
| 6,059,011 A | 5/2000 | Giolo |
| 6,083,255 A | 7/2000 | Laufer et al. |
| 6,099,251 A | 8/2000 | Lafleur |
| 6,102,037 A | 8/2000 | Koch |
| 6,113,722 A | 9/2000 | Hoffman et al. |
| 6,130,671 A | 10/2000 | Argiro |
| 6,131,570 A | 10/2000 | Schuster et al. |
| 6,139,571 A | 10/2000 | Fuller et al. |
| 6,156,036 A | 12/2000 | Sussman et al. |
| 6,162,232 A | 12/2000 | Shadduck |
| 6,179,805 B1 | 1/2001 | Sussman et al. |
| 6,194,066 B1 | 2/2001 | Hoffman |
| 6,200,333 B1 | 3/2001 | Laufer |
| 6,210,404 B1 | 4/2001 | Shadduck |
| 6,219,059 B1 | 4/2001 | Argiro |
| 6,273,907 B1 | 8/2001 | Laufer |
| 6,283,988 B1 | 9/2001 | Laufer et al. |
| 6,299,633 B1 | 10/2001 | Laufer |
| 6,300,150 B1 | 10/2001 | Venkatasubramanian |
| 6,312,474 B1 | 11/2001 | Francis et al. |
| 6,327,505 B1 | 12/2001 | Medhkour et al. |
| 6,394,949 B1 | 5/2002 | Crowley et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,411,852 B1 | 6/2002 | Danek et al. |
| 6,458,231 B1 | 10/2002 | Wapner et al. |
| 6,468,313 B1 | 10/2002 | Claeson et al. |
| 6,488,673 B1 | 12/2002 | Laufer et al. |
| 6,493,589 B1 | 12/2002 | Medhkour et al. |
| 6,508,816 B2 | 1/2003 | Shadduck |
| 6,527,761 B1 | 3/2003 | Soltesz et al. |
| 6,575,929 B2 | 6/2003 | Sussman et al. |
| 6,579,270 B2 | 6/2003 | Sussman et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,652,594 B2 | 11/2003 | Francis et al. |
| 6,653,525 B2 | 11/2003 | Ingenito et al. |
| 6,669,694 B2 | 12/2003 | Shadduck |
| 6,676,628 B2 | 1/2004 | Sussman et al. |
| 6,679,264 B1 | 1/2004 | Deem et al. |
| 6,682,520 B2 | 1/2004 | Ingenito |
| 6,692,494 B1 | 2/2004 | Cooper et al. |
| 6,712,812 B2 | 3/2004 | Roschak et al. |
| 6,719,738 B2 | 4/2004 | Mehier |
| 6,755,794 B2 | 6/2004 | Soukup |
| 6,770,070 B1 | 8/2004 | Balbierz |
| 6,776,765 B2 | 8/2004 | Soukup et al. |
| 6,860,847 B2 | 3/2005 | Alferness et al. |
| 6,885,888 B2 | 4/2005 | Rezai |
| 6,901,927 B2 | 6/2005 | Deem et al. |
| 6,904,909 B2 | 6/2005 | Deem et al. |
| 6,907,881 B2 | 6/2005 | Suki et al. |
| 6,911,028 B2 | 6/2005 | Shadduck |
| 6,986,769 B2 | 1/2006 | Nelson et al. |
| 6,997,189 B2 | 2/2006 | Biggs et al. |
| 7,022,088 B2 | 4/2006 | Keast et al. |
| 7,027,869 B2 | 4/2006 | Danek et al. |
| 7,031,504 B1 | 4/2006 | Argiro et al. |
| 7,083,612 B2 | 8/2006 | Littrup et al. |
| 7,128,748 B2 | 10/2006 | Mooradian et al. |
| 7,136,064 B2 | 11/2006 | Zuiderveld |
| 7,144,402 B2 | 12/2006 | Kuester et al. |
| 7,144,588 B2 | 12/2006 | Nicholas et al. |
| 7,174,644 B2 | 2/2007 | Critelli et al. |
| 7,175,644 B2 | 2/2007 | Cooper et al. |
| 7,192,400 B2 | 3/2007 | Campbell et al. |
| 7,198,635 B2 | 4/2007 | Danaek et al. |
| 7,233,820 B2 | 6/2007 | Gilboa |
| 7,235,070 B2 | 6/2007 | Vanney |
| 7,335,195 B2 | 2/2008 | Mehier |
| 7,347,859 B2 | 3/2008 | Garabedian et al. |
| 7,412,977 B2 | 8/2008 | Fields et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,462,162 B2 | 12/2008 | Phan et al. |
| 7,628,789 B2 | 12/2009 | Soltesz et al. |
| 7,708,712 B2 | 5/2010 | Phan et al. |
| 7,740,017 B2 | 6/2010 | Danek et al. |
| 7,756,563 B2 | 7/2010 | Higgins et al. |
| 7,778,704 B2 | 8/2010 | Rezai et al. |
| 7,815,590 B2 | 10/2010 | Cooper |
| 7,819,908 B2 | 10/2010 | Ingenito |
| 7,889,905 B2 | 2/2011 | Higgins et al. |
| 7,906,124 B2 | 3/2011 | Laufer et al. |
| 7,913,698 B2 | 3/2011 | Barry et al. |
| 7,985,187 B2 | 7/2011 | Wibowo et al. |
| 7,993,323 B2 | 8/2011 | Barry et al. |
| 8,002,740 B2 | 8/2011 | Willink et al. |
| 8,088,127 B2 | 1/2012 | Mayse et al. |
| 8,147,532 B2 | 4/2012 | Barry et al. |
| 8,172,827 B2 | 5/2012 | Deem et al. |
| 8,187,269 B2 | 5/2012 | Shadduck et al. |
| 8,251,070 B2 | 8/2012 | Danek et al. |
| 8,292,882 B2 | 10/2012 | Danek et al. |
| 8,322,335 B2 | 12/2012 | Barry et al. |
| 8,409,167 B2 | 4/2013 | Roschak |
| 8,444,636 B2 | 5/2013 | Shadduck et al. |
| 8,585,645 B2 | 11/2013 | Barry et al. |

(56) References Cited

U.S. PATENT DOCUMENTS

| | | | |
|---|---|---|---|
| 8,608,724 B2 | 12/2013 | Roschak | |
| 8,628,495 B2 | 1/2014 | Horton et al. | |
| 8,709,034 B2 | 4/2014 | Keast et al. | |
| 8,734,380 B2 | 5/2014 | Barry et al. | |
| 8,784,400 B2 | 7/2014 | Roschak | |
| 8,858,549 B2 | 10/2014 | Shadduck et al. | |
| 8,900,223 B2 | 12/2014 | Shadduck | |
| 9,037,215 B2 | 5/2015 | Higgins et al. | |
| 9,050,076 B2 | 6/2015 | Barry et al. | |
| 9,133,858 B2 | 9/2015 | Macchia et al. | |
| 9,265,468 B2 | 2/2016 | Rai et al. | |
| 9,393,396 B2 | 7/2016 | Peyman | |
| 9,913,969 B2 | 3/2018 | Roschak | |
| 10,064,697 B2 | 9/2018 | Sharma et al. | |
| 2002/0077516 A1 | 6/2002 | Flanigan | |
| 2002/0111386 A1 | 8/2002 | Michael et al. | |
| 2002/0112723 A1 | 8/2002 | Schuster et al. | |
| 2002/0177846 A1* | 11/2002 | Mulier | A61B 18/04 606/27 |
| 2003/0055331 A1 | 3/2003 | Kotmel et al. | |
| 2003/0099279 A1 | 5/2003 | Venkatasubramanian et al. | |
| 2003/0139789 A1* | 7/2003 | Tvinnereim | A61B 18/1485 607/99 |
| 2003/0181922 A1 | 9/2003 | Alferness | |
| 2003/0233099 A1 | 12/2003 | Danaek et al. | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0055606 A1 | 3/2004 | Hendricksen et al. | |
| 2004/0068306 A1 | 4/2004 | Shadduck | |
| 2004/0131587 A1 | 7/2004 | Thomas et al. | |
| 2004/0199226 A1 | 10/2004 | Shadduck | |
| 2004/0200484 A1 | 10/2004 | Springmeyer | |
| 2004/0244803 A1 | 12/2004 | Tanaka | |
| 2005/0016530 A1* | 1/2005 | McCutcheon | A61B 17/12159 128/200.24 |
| 2005/0066974 A1 | 3/2005 | Fields et al. | |
| 2005/0166925 A1 | 8/2005 | Wilson et al. | |
| 2005/0171396 A1 | 8/2005 | Pankratov et al. | |
| 2005/0171582 A1 | 8/2005 | Matlock | |
| 2005/0203483 A1 | 9/2005 | Perkins et al. | |
| 2005/0215991 A1 | 9/2005 | Altman et al. | |
| 2005/0222485 A1 | 10/2005 | Shaw et al. | |
| 2006/0004400 A1 | 1/2006 | Mcgurk et al. | |
| 2006/0047291 A1 | 3/2006 | Barry | |
| 2006/0100619 A1 | 5/2006 | Mcclurken et al. | |
| 2006/0130830 A1 | 6/2006 | Barry | |
| 2006/0135955 A1 | 6/2006 | Shadduck | |
| 2006/0161233 A1* | 7/2006 | Barry | A61M 16/14 607/113 |
| 2006/0162731 A1 | 7/2006 | Wondka et al. | |
| 2006/0200076 A1 | 9/2006 | Gonzalez et al. | |
| 2006/0224154 A1 | 10/2006 | Shadduck et al. | |
| 2007/0032785 A1 | 2/2007 | Diederich et al. | |
| 2007/0036417 A1 | 2/2007 | Argiro et al. | |
| 2007/0068530 A1 | 3/2007 | Pacey | |
| 2007/0091087 A1 | 4/2007 | Zuiderveld | |
| 2007/0092864 A1 | 4/2007 | Reinhardt et al. | |
| 2007/0102011 A1 | 5/2007 | Danek et al. | |
| 2007/0106292 A1 | 5/2007 | Kaplan et al. | |
| 2007/0109299 A1 | 5/2007 | Peterson | |
| 2007/0112349 A1 | 5/2007 | Danek et al. | |
| 2007/0118184 A1 | 5/2007 | Danek et al. | |
| 2007/0137646 A1 | 6/2007 | Weinstein et al. | |
| 2007/0293853 A1 | 12/2007 | Truckai et al. | |
| 2008/0033493 A1 | 2/2008 | Deckman et al. | |
| 2008/0132826 A1 | 6/2008 | Shadduck et al. | |
| 2009/0018538 A1 | 1/2009 | Webster et al. | |
| 2009/0043301 A1 | 2/2009 | Jarrard et al. | |
| 2009/0118538 A1 | 5/2009 | Pizzocaro et al. | |
| 2009/0138001 A1 | 5/2009 | Barry et al. | |
| 2009/0149846 A1 | 6/2009 | Hoey et al. | |
| 2009/0149897 A1 | 6/2009 | Dacey, Jr. et al. | |
| 2009/0156895 A1 | 6/2009 | Higgins et al. | |
| 2009/0192508 A1 | 7/2009 | Laufer et al. | |
| 2009/0216220 A1 | 8/2009 | Hoey et al. | |
| 2009/0301483 A1 | 12/2009 | Barry et al. | |
| 2009/0306640 A1 | 12/2009 | Glaze et al. | |
| 2009/0306644 A1 | 12/2009 | Mayse et al. | |
| 2009/0312753 A1 | 12/2009 | Shadduck | |
| 2010/0094270 A1 | 4/2010 | Sharma | |
| 2010/0185087 A1* | 7/2010 | Nields | A61B 6/0492 600/439 |
| 2010/0204688 A1* | 8/2010 | Hoey | A61B 18/04 606/27 |
| 2010/0256714 A1 | 10/2010 | Springmeyer | |
| 2010/0262133 A1 | 10/2010 | Hoey et al. | |
| 2010/0310146 A1 | 12/2010 | Higgins et al. | |
| 2011/0077628 A1 | 3/2011 | Hoey et al. | |
| 2011/0118725 A1 | 5/2011 | Mayse et al. | |
| 2011/0160648 A1 | 6/2011 | Hoey | |
| 2011/0172654 A1 | 7/2011 | Barry et al. | |
| 2011/0257644 A1 | 10/2011 | Barry et al. | |
| 2011/0270031 A1 | 11/2011 | Frazier et al. | |
| 2011/0301587 A1 | 12/2011 | Deem et al. | |
| 2012/0016363 A1 | 1/2012 | Mayse et al. | |
| 2012/0016364 A1 | 1/2012 | Mayse et al. | |
| 2012/0289776 A1 | 11/2012 | Keast et al. | |
| 2013/0006231 A1* | 1/2013 | Sharma | A61B 5/1076 606/27 |
| 2013/0267939 A1 | 10/2013 | Barry et al. | |
| 2013/0324987 A1 | 12/2013 | Leung et al. | |
| 2014/0025057 A1 | 1/2014 | Hoey et al. | |
| 2014/0088669 A1* | 3/2014 | Lanphere | A61P 9/10 607/96 |
| 2014/0163664 A1* | 6/2014 | Goldsmith | A61B 17/12181 623/1.11 |
| 2014/0275952 A1 | 9/2014 | Monroe et al. | |
| 2014/0276713 A1 | 9/2014 | Hoey et al. | |
| 2015/0094607 A1 | 4/2015 | Barry et al. | |
| 2015/0230852 A1 | 8/2015 | Barry et al. | |
| 2016/0008050 A1* | 1/2016 | Rajagopalan | A61B 18/14 606/28 |
| 2016/0180529 A1 | 6/2016 | Rai et al. | |
| 2016/0220297 A1 | 8/2016 | Kroon et al. | |
| 2016/0310200 A1 | 10/2016 | Wang | |
| 2017/0172640 A1 | 6/2017 | Henne | |
| 2018/0055495 A1* | 3/2018 | Tehrani | A61B 10/04 |
| 2018/0318002 A1 | 11/2018 | Barry et al. | |
| 2019/0069948 A1 | 3/2019 | Herth et al. | |
| 2019/0343579 A1 | 11/2019 | Tandri et al. | |

FOREIGN PATENT DOCUMENTS

| | | | |
|---|---|---|---|
| EP | 1143864 B1 | 2/2004 | |
| EP | 1173103 B1 | 10/2005 | |
| EP | 1326549 B1 | 12/2005 | |
| EP | 1326548 B1 | 1/2006 | |
| EP | 1485033 B1 | 8/2009 | |
| WO | 0011927 A2 | 3/2000 | |
| WO | 0102042 A1 | 1/2001 | |
| WO | 02069821 A1 | 9/2002 | |
| WO | 03070302 A1 | 8/2003 | |
| WO | 03086498 A2 | 10/2003 | |
| WO | 2005025635 A2 | 3/2005 | |
| WO | 2005102175 A2 | 11/2005 | |
| WO | 2006003665 A2 | 1/2006 | |
| WO | 2006052940 A2 | 5/2006 | |
| WO | 2006053308 A2 | 5/2006 | |
| WO | 2006053309 A2 | 5/2006 | |
| WO | 2006080015 A2 | 8/2006 | |
| WO | 2006116198 A2 | 11/2006 | |
| WO | 2008051706 A2 | 5/2008 | |
| WO | WO-2008064026 A2 * | 5/2008 | A61B 18/04 |
| WO | 2009009236 A1 | 1/2009 | |
| WO | 2009009398 A1 | 1/2009 | |
| WO | 2009015278 A1 | 1/2009 | |
| WO | WO-2009009398 A1 * | 1/2009 | A61B 18/04 |
| WO | 2009137819 A1 | 11/2009 | |
| WO | 2010042461 A1 | 4/2010 | |
| WO | 2011056684 A2 | 5/2011 | |

(56) References Cited

FOREIGN PATENT DOCUMENTS

| WO | 2011060200 A1 | 5/2011 |
|---|---|---|
| WO | 2011060201 A1 | 5/2011 |
| WO | 2011127216 A2 | 10/2011 |

OTHER PUBLICATIONS

Blacker, G. F.; Vaporization of the uterus; J. of Obstetrics and Gynaecology; vol. 33; pp. 488-511; 1902.
Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.
clinical trials.gov.; Study of the AeriSeal System for Hyperinflation Reduction in Emphysema; 4 pages; Nov. 5, 2014; retrieved from the internet (http://clinicaltrials.gov/show/NCT01449292).
Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).
Cox et al., "Bronchial Thermoplasty for Asthma." American Journal of Respiratory Critical Care Medicine 173: 965-969 (2006).
Delaunois; Anatomy and physiology of collateral respiratory pathways; Eur. Respir. J.; 2(9); pp. 893-904; Oct. 1989.
Eyal et al.; The acute effect of pulmonary burns on lung mechanics and gas exchange in the rabbit; Br. J. Anaesth.; vol. 47; pp. 546-552; (year of publication is sufficiently earlier than the effective U.S. filing date and any foreign priority date) 1975.
Ferlay et al.; GLOBOCAN 2008 v1.2, Cancer Incidence and Mortality Worldwide: IARC CancerBase No. 10 [internet]; 16 pages; retrieved from the Internet (http://www.iarc.fr/en/media-centre/iarcnews/2010/GLOBOCAN2008.pdf); Lyon, France: International Agency for Research on Cancer; Jun. 1, 2010.
Fishman et al., A randomized trial comparing lung-volume-reduction surgery with medical therapy for severe emphysema, N Engl J Med, vol. 348, No. 21, pp. 2059-2073, May 22, 2003.
Goldberg et al.; Radiofrequency tissue ablation in the rabbit lung: Efficacy and complications; Acad. Radiol.; vol. 2; pp. 776-784; Sep. 1995.
Henne et al.; U.S. Appl. No. 14/957,433 entitled "Vapor treatment of lung nodules and tumors," filed Dec. 2, 2015.
Herth et al.; Efficacy predictors of lung volume reduction with zephyr valves in a european cohort; Eur. Respir. J.; 39(6); pp. 1334-1342; Jun. 2012.
Homasson, et al., "Bronchoscopic cryotherapy for airway strictures caused by tumors," Chest, vol. 90, No. 2, pp. 159-164, Aug. 1986.
Kang, Li, "Efficient optimal net surface detection for image segmentation—from theory to practice," M.Sc. Thesis, The University of Iowa, Dec. 2003.
Kinsella et al.; Quantitation of emphysema by computed tomography using a "densitymask" program and correlation with pulmonary function tests; Chest; 97(2); pp. 315-321; Feb. 1990.
Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.
Marasso, et al., "Cryosurgery in bronchoscopic treatment of tracheobronchial stenosis," Chest, vol. 103, No. 2, pp. 472-474, Feb. 1993.
Marasso, et al., "Radiofrequency resection of bronchial tumours in combination with cryotherapy: evaluation of a new technique," Thorax, vol. 53, pp. 106-109, (year of publication is sufficiently earlier than the effective U.S. filing date and any foreign priority date) 1998.
Mathur et al., Fiberoptic bronchoscopic cryotherapy in the management of tracheobronchial obstruction, Chest, vol. 110, No. 3, pp. 718-723, Sep. 1996.
Morice et al.; Endobrinchial argon plasma coagulation for treatment of hemotysis and neoplastic airway obstruction, Chest, vol. 119, No. 3, pp. 781-787, Mar. 2001.
Moritz et al.; The effects of inhaled heat on the air pasage and lungs; American Journal of Pathology; vol. XXI; pp. 311-331; (year of publication is sufficiently earlier than the effective U.S. filing date and any foreign priority date) 1944.
Moulding et al.; Preliminary studies for achieving transcervical oviduct occlusion by hot water or low-pressure steam; Advances in Planned Parenthood; vol. 12, No. 2; pp. 79-85; (year of publication is sufficiently earlier than the effective U.S. filing date and any foreign priority date) 1977.
National Lung Screening Trial Research Team; Reduced lung-cancer mortality with low-dose computed tomographic screening; N. Eng. J. Med.; 365(5); pp. 395-409; Aug. 4, 2011.
Pieter et al.; U.S. Appl. No. 15/013,748 entitled "Medical vapor generator," filed Feb. 2, 2016.
Pracht, Adam, "VIDA takes new approach," Iowa City Press-Citizen, Sep. 12, 2005.
Quin, Jacquelyn, "Use of neodymium yttrium aluminum garnet laser in long-term palliation of airway obstruction," Connecticut Medicine, vol. 59, No. 7, pp. 407-412, Jul. 1995.
Sciurba et al.; A randomized study of endobronchial valves for advanced emphysema; N. Eng. J. Med.; 363(13); pp. 1233-1244; Sep. 23, 2010.
Shah et al.; Collateral ventilation and selection of techniques for bronchoscopic lung volume reduction; Thorax; 67(4); pp. 285-286; Apr. 2012.
Slebos et al.; Bronchoscopic lung volume reduction coil treatment of patients with severe heterogeneous emphysema; Chest; 142(3); pp. 574-582; Sep. 2012.
Sutedja, et al.; Bronchoscopic treatment of lung tumors; Elsevier, Lung Cancer, 11, pp. 1-17, Jul. 1994.
Tschirren et al.; Intrathoracic airway trees: segmentation and airway morphology analysis from low-dose CT scans; IEEE Trans. Med. Imaging; vol. 24, No. 12; pp. 1529-1539; Dec. 2005.
Tschirren, Juerg; Segmentation, anatomical labeling, branchpoint matching, and quantitative analysis of human airway trees in volumetric CT images; Ph.D. Thesis; The University of Iowa; Aug. 2003.
Tschirren, Juerg; Segmentation, anatomical labeling, branchpoint matching, and quantitative analysis of human airway trees in volumetric CT images; Slides from Ph.D. defense; The University of Iowa; Jul. 10, 2003.
Van De Velde; Vapo-cauterization of the uterus; Amer. J. Med. Sci.; vol. CXVIII; (year of publication is sufficiently earlier than the effective U.S. filing date and any foreign priority date) 1899.
Vorre et al.; Morphology of tracheal scar after resection with CO2-laser and high-frequency cutting loop; Acta Otolaryngol (Stockh); vol. 107; pp. 307-312; (year of publication is sufficiently earlier than the effective U.S. filing date and any foreign priority date) 1989.

\* cited by examiner

BRONCHOSCOPIC MULTIMODALITY LUNG TUMOR TREATMENT

CROSS-REFERENCE TO RELATED APPLICATIONS

This application claims the benefit of provisional patent application No. 62/556,785, filed Sep. 11, 2017, entitled "BRONCHOSCOPIC MULTIMODALITY LUNG TUMOR TREATMENT", incorporated by reference herein in its entirety.

BACKGROUND OF THE INVENTION

The present invention relates to medical methods for treating lung tumors, and more specifically to minimally invasive medical methods for ablating lung tumors.

Bronchoscopic radio frequency ablation and bronchoscopic thermal vapor ablation are examples of minimally invasive techniques to treat lung tumors in a patient.

Bronchoscopic radio frequency ablation involves navigating an ablation catheter through the airways of the patient and to the lung tumor. The ablation catheter is activated, delivering radio frequency energy to the tumor. The physician targets or focuses the energy towards the center of the tumor to minimize damage to healthy tissue adjacent the tumor.

A drawback of radio frequency ablation is that targeting the center of the lung tumor risks allowing the margin of the tumor to remain untreated. This is undesirable.

Increasing the energy delivered to the tumor, however, is also undesirable due to the likelihood of overheating the healthy tissue adjacent the tumor.

Another drawback of bronchoscopic radio frequency ablation arises from the structural limitations of the ablation electrodes and the available spacing to maneuver the electrodes. To compensate, the physician may elect to increase the energy delivered to the target. Increasing the energy delivered to the target tissue, however, risks causing collateral damage to healthy adjacent tissue.

Bronchoscopic thermal vapor ablation is another technique to treat lung tumors. Bronchoscopic thermal ablation sends a condensable vapor across the lung tumor. The vapor, upon contact with tissue, changes phase from gas to liquid, heating the outside of the lung tumor and ultimately serving to ablate the tumor. Bronchoscopic thermal vapor ablation heats the tumor from the outside to the inside. A challenge with bronchoscopic thermal vapor ablation is to quickly reach the center or inside of the lung tumor. Increasing the thermal energy delivered via the vapor is undesirable for risking collateral damage to healthy adjacent tissue.

Notwithstanding the above, minimally invasive methods and systems are still desired that effectively ablate lung tumors in a patient, and to do so without damaging the healthy adjacent tissue and without putting the patient at any further risk of infection. Accordingly, a method that overcomes the above mentioned challenges is desirable.

SUMMARY OF THE INVENTION

The present invention is a method for treating a suspect tissue mass such as, for example, a lung tumor or metastasis.

A minimally invasive medical technique for treating lung tumors includes use of multiple ablation modalities in a single procedure. Condensable vapor ablation and electrosurgical ablation are applied to treat the surface of the tumor and to debulk inner regions of the tumor, respectively.

In embodiments, a method of treating a suspect tissue mass in a lung comprises uniformly applying heat to the margin or exterior of the suspect tissue mass and discretely applying heat to interior portions of the suspect tissue mass.

In embodiments, the step of uniformly applying heat to the margin of the suspect tissue mass comprises delivering a condensable vapor around the suspect tissue mass.

In embodiments, the step of discretely applying heat to the interior of the suspect tissue mass comprises advancing an electrosurgical instrument into direct contact with the suspect tissue mass, and activating the instrument.

In embodiments, the step of discretely applying heat to the interior of the suspect tissue mass comprises placing a heat source at a discrete internal location (e.g., the center of the suspect tissue mass), and radiating heat from the heat source towards the exterior of the mass.

In embodiments, the electrosurgical instrument is an RF energy catheter.

In embodiments, the method further comprises assessing an exterior of the suspect tissue mass for uniformity prior to the step of heating by the first modality, and assessing an interior of the suspect tissue mass for density prior to the step of heating by the second modality. The steps of assessing may be performed preoperatively using CT or other imaging data, and analysis. Additionally, the step of assessing may be performed using ultrasound, bronchoscope or other diagnostic and imaging techniques. Should the suspect tissue mass be non-uniform or lack symmetry, heating is performed by delivering condensable vapor. The second modality is then carried out to heat from the inside out. In embodiments, the method further comprises monitoring a first ablation region growing inward and a second ablation region growing outward arising from the first modality and second modality of heating, respectively, and confirming an overlap zone between the first ablation region and second ablation region.

Still other descriptions, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Method Overview

Figure 1:
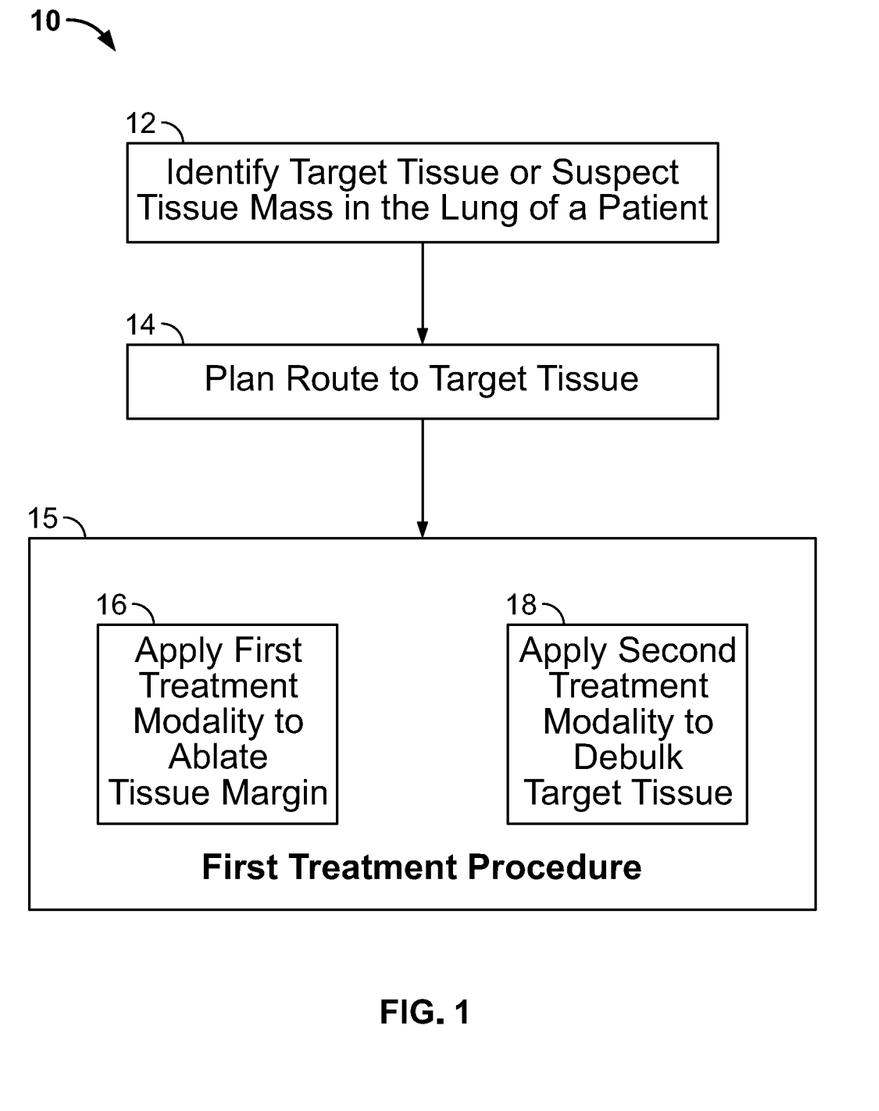
FIG. 1 a flow chart illustrating a method in accordance with one embodiment of the present invention.

An overview of a lung tumor treatment method 10 in accordance with embodiments of the present invention is illustrated in FIG. 1.

Step 12 states to identify a lung tumor or suspect tissue mass in the lung of the patient. By "suspect tissue mass", it is meant a tissue mass whether diseased or otherwise a candidate for diagnosis, treatment or removal. Examples of a suspect tissue mass include, without limitation, a tumor, metastasis, growth, lymph node, tissue nodule, or other diseased tissue causing obstructions in the lung. Also, by "diseased lung tissue" it is meant a disorder or function in the lung tissue including, without limitation, emphysema, lung cancer or metastasis, TB, aspergillus, and pneumonia.

Physicians may identify the suspect tissue mass using imaging technology including, for example, CT scans, fluoroscopy, X-rays, and bronchoscopy.

Step 14 states to plan a route to the target tissue, e.g., the lung tumor. Though a physician may plan a route to the tumor by eye using the X-ray or video images of the lung and tumor, more sophisticated techniques automatically compute an optimal route to the target through the airways. Examples of airways include the trachea, bronchi, bronchial branches including, without limitation, the bronchioles and terminal bronchioles. Examples of route planning techniques are described in U.S. Pat. No. 9,037,215.

The next step shown in FIG. 1 is the first treatment procedure 15. By "first treatment procedure", it is meant a single continuous medical operation or intervention without interruption (such as by patient discharge from the OR, hospital, or surgery center) and regardless of how many individual treatment modalities, described below, are performed on the patient during her first treatment procedure.

Step 16 states to apply a first treatment modality to ablate the tissue margin. The first treatment modality serves to ablate across the exterior surface of the lung tumor. As will be described further herein, an exemplary first modality treatment for ablating the tumor margin includes, without limitation, condensable vapor ablation. By "margin of the tumor" it is meant the outer region or boundary of the tumor. Examples of the margin of the tumor include the outer limits, boundary, outside, and periphery of the tumor.

Step 18 states to apply a second treatment modality to debulk target tissue. As will described further herein, an instrument is advanced along the route to the target tissue. Once the position of the working tip is confirmed, energy is applied to debulk the lung tumor. Exemplary techniques to debulk the lung tumor include, without limitation, electrosurgery, microwave ablation, and cryosurgery.

Figure 2:
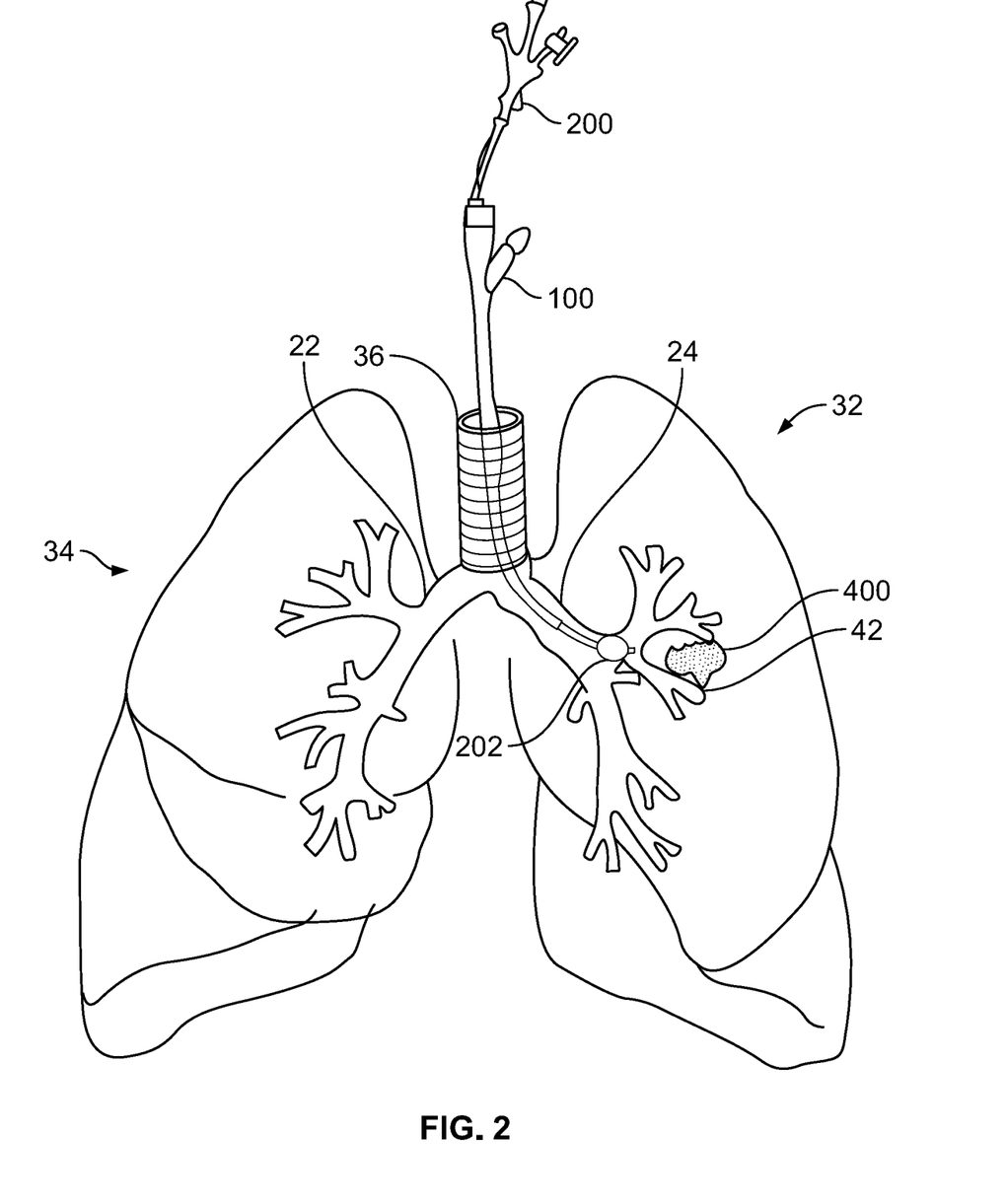
FIGS. 2 and 3 are illustrations of a method for delivering a condensable vapor to ablate a lung tumor in accordance with one embodiment of the invention.
Figure 3:
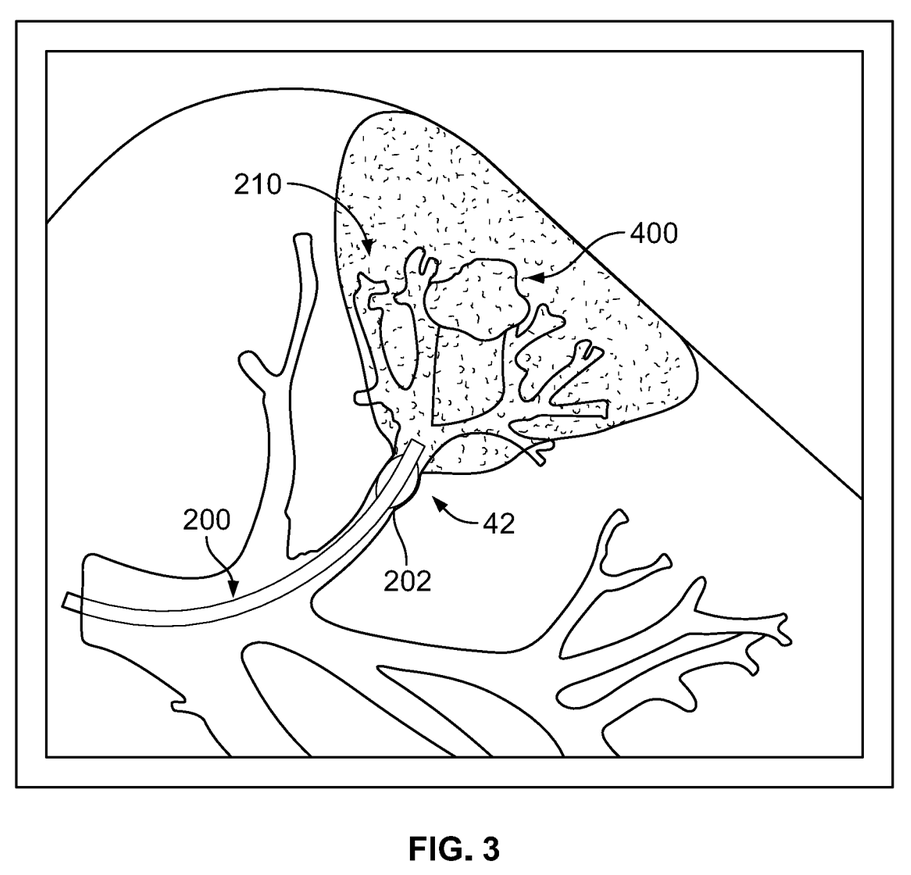

With reference to FIGS. 2 and 3 aspects of the invention are described in further detail. Particularly, FIG. 2 shows the respiratory system including the trachea 36, left lung lobe 32 and right lung lobe 34, left bronchi 24 and right bronchi 22 and lobar bronchial branches. The lobar bronchial branches further break off into segmental and sub-segmental branches. A lung tumor 400 is shown in the left lobe 32 in the vicinity of the left secondary bronchi 42 or segmental bronchi.

Bronchoscopic Condensable Vapor Ablation

FIG. 2 also illustrates a bronchoscope 100 having a working channel extending through the trachea 36 and into the left bronchi 24. Guidance of the bronchoscope to the target area in the lung may be performed by eye using the video monitor (not shown), under fluoroscopy, or using navigation or guidance systems. Examples of guidance and navigation systems are described in the U.S. Pat. Nos. 7,889,905 and 7,756,563.

Vapor ablation catheter 200 is shown advanced through the bronchoscope 100 and into the bronchi branch upstream or proximal to the lung tumor 400. Balloon 202 is inflated to isolate the target airways and tumor.

With reference to FIG. 3, a condensable vapor 210 is delivered from the end of the catheter 200 into the airways and tumor 400. The vapor surrounds or engulfs the tumor, quickly heating the tumor as the vapor changes to liquid phase. The margin of the tumor is initially heated by thermal convection, and then heat thermally conducts towards the center of the tumor until the tumor is ablated. In a sense, the tumor 400 is heated from the outside to the inside (namely, "outside in").

An advantage of vapor ablation is that a wide range of tissue geometries may be treated because of the gaseous nature of the vapor. The catheter is not required to contact the target tissue. The vapor crosses any gaps present in the tissue until the tumor is completely engulfed or encapsulated by the vapor. Additionally, porous tissues near the tumor margin can be permeated by the vapor, and ablated.

The energy delivery or vapor ablation catheter 200 may have various configurations. Examples of vapor ablation catheters, energy generators and controllers are described in U.S. Pat. Nos. 7,913,698; 8,585,645, and US Patent Publication No. 2016/0151103. In some embodiments, the catheter is adapted to detachably couple to an energy generator (not shown).

Electrosurgical Ablation

Figure 4:
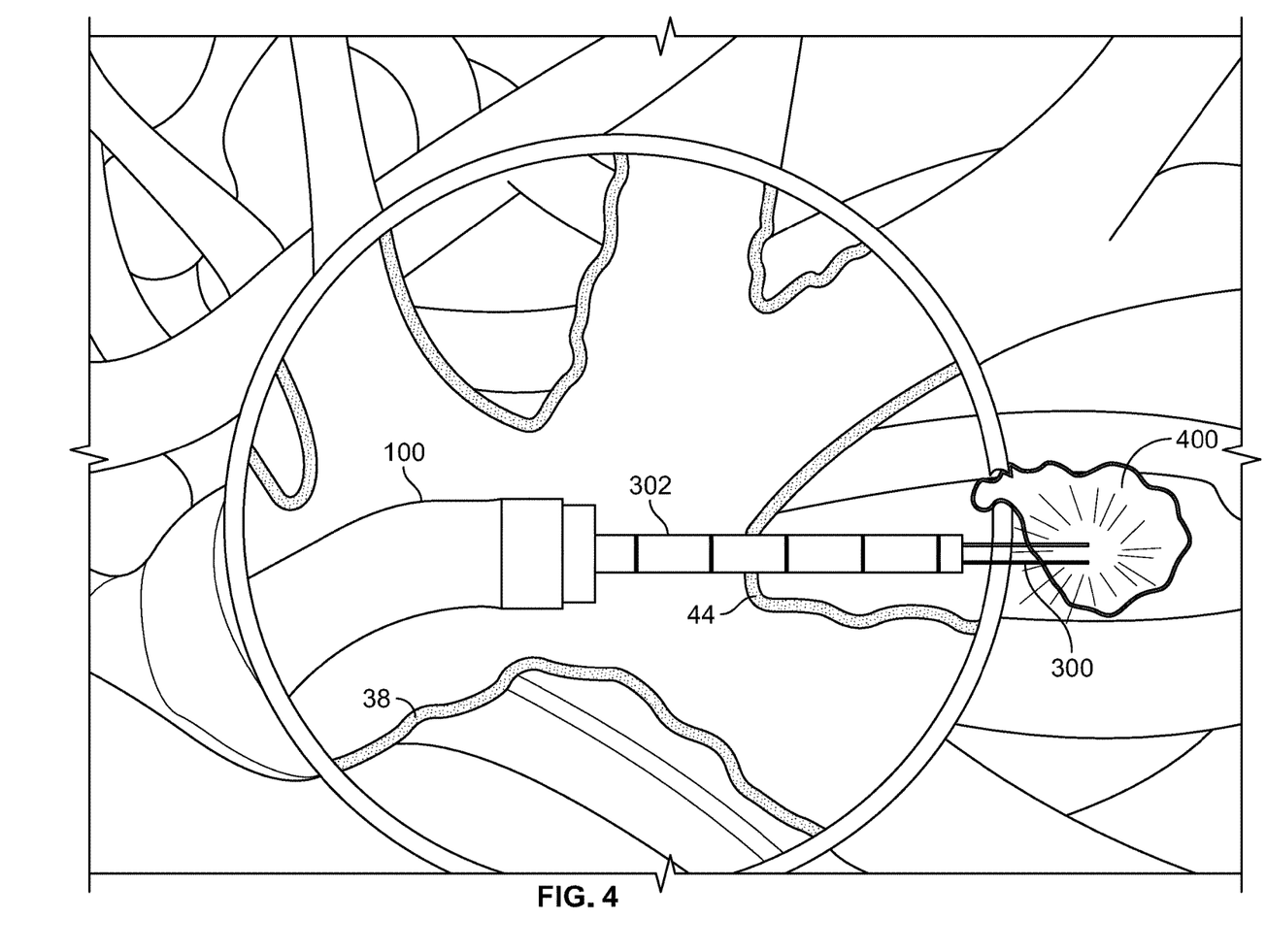
FIG. 4 is an illustration of a method for ablating a lung tumor by applying radio frequency energy in accordance with one embodiment of the invention.

As stated above, embodiments of the invention include treatment of a lung tumor with a second treatment modality such as, for example, radio frequency ablation. With reference to FIG. 4, a radio frequency probe 300 is shown advanced beyond the end of a sheath 302, and into the lung tumor 400. Although the distal tip of the electrosurgical instrument 300 is shown penetrating the tumor 400, the invention is not so limited. Embodiments of the invention include, without limitation, making mere contact with the tumor, or partially inserting the tip, or contacting a pole or edge of the tumor.

Once the physician confirms the catheter tip 300 or RF electrode is properly positioned, the radio frequency catheter is activated. Position confirmation or tracking of the catheters can be performed by a wide range of guidance and location techniques including, without limitation, fluoroscopy or use of electromagnetic sensors. Examples of tracking and guidance techniques are described in U.S. Pat. Nos. 6,380,732 and 9,265,468 and US Patent Publication no. 2016/0180529.

In embodiments, and with reference to FIG. 4, the tip 300 is a sharp needle pair and penetrates the lung tumor 400. The electrodes act as a heat source and initially heat the tissue where the electrodes make contact. The heat thermally conducts through the tumor from the heat source. When the tip is positioned within the tumor, the tumor is ablated from the heat source (or point) to the exterior (namely, "inside out").

An advantage of RF ablation is that the central denser portion of the tumor can be efficiently ablated. This is particularly useful for larger tumors where the heat from the vapor ablation, described above, may take longer to reach the dense central portions of the tumor. RF ablation is effective to ablate dense tissues and to debulk large volumes of tissue compared to other modalities. In contrast, condensable vapor ablation is effective to ablate across an entire surface where the geometry of the surface may be non-uniform and less dense than the central portions of the tumor.

The radio frequency energy delivery catheter may take a wide range of configurations and the electrode shape itself may also vary widely. Examples of electrode shapes include, without limitation, needle, hook, basket, loop, helix, coil, forceps or clamp, tubular, and snare or lasso. The electrode distal section may also be configured to flex, turn, and steer using mechanical or thermal action. Examples of RF ablation catheters, energy generators, and controllers are described in U.S. Pat. Nos. 6,692,494; 7,022,088 and US Patent Publication No. 2013/0046296.

Additional modalities to abate the tumor may include catheters and probes configured to deliver microwave energy, cryo-energy, or other types of energy suited to ablate lung tumors.

Figure 5:
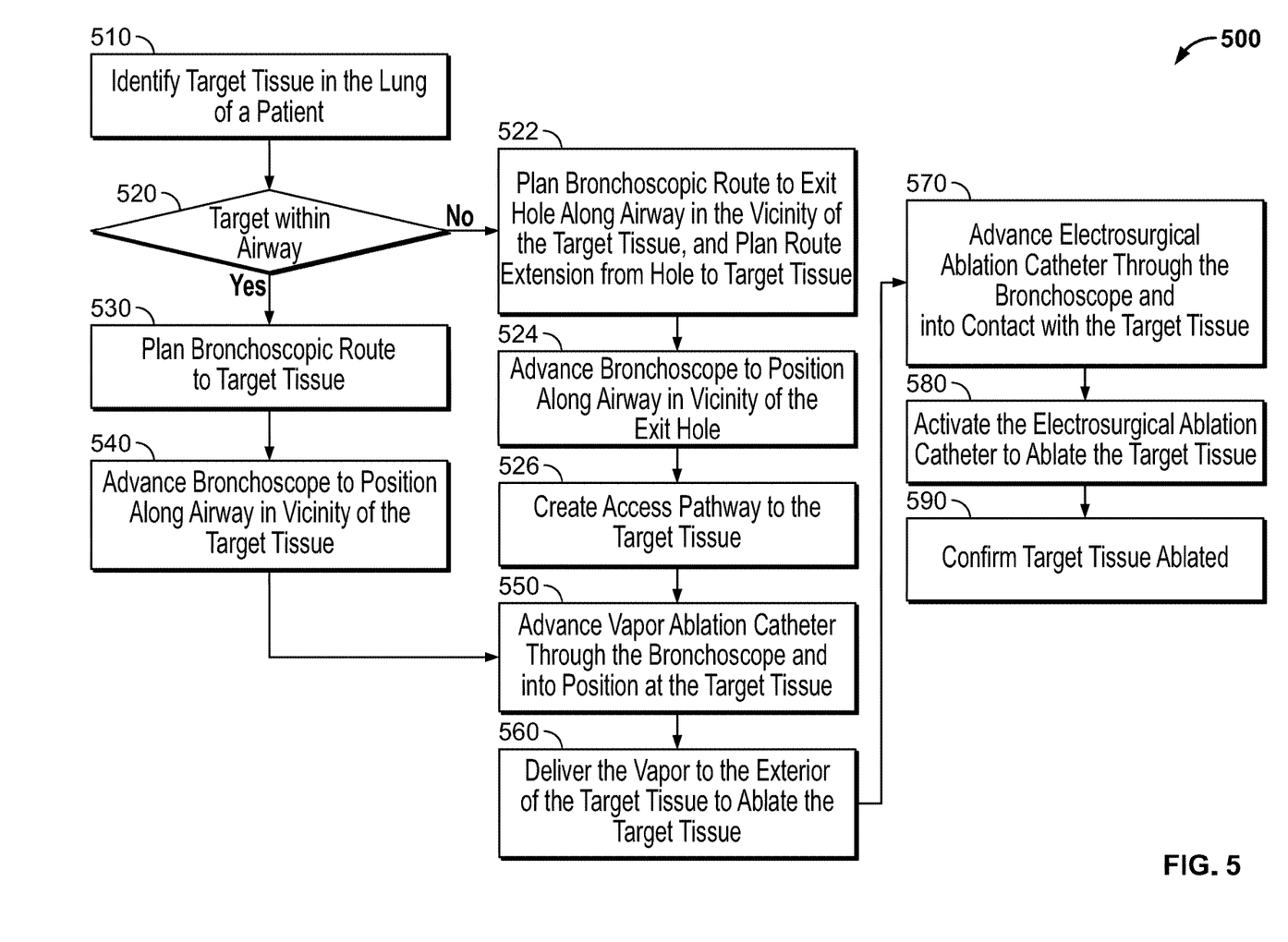
FIG. 5 is a flow chart illustrating another method to treat a lung tumor outside of an airway in the lung of a patient.

FIG. 5 is a flow chart of another method 500 for treating tumors in accordance with embodiments of the present invention.

Similar to the method described above, step 510 states to identify the tumor in the lung of a patient. Step 510 may be performed as described above.

Step 520 queries whether the target is within an airway. If yes, the procedure may proceed substantially as outlined above in connection with the methods described above.

Particularly, step 530 states to plan the bronchoscopic route to the target tissue.

Step 540 states to advance the bronchoscope to a position along the airway in the vicinity of the target tissue, preferably with a clear view of the target to be ablated.

Step 550 states to advance the vapor ablation catheter through the bronchoscope and into position at the target tissue. The position of the catheter may be confirmed as described above.

Step 560 states to deliver condensable vapor to the exterior of the target tissue to ablate the target tissue. After treatment with the vapor, the vapor catheter is withdrawn from the patient.

Step 570 states to advance the electrosurgical ablation catheter through the bronchoscope and into contact with the target tissue. Position of the catheter may be confirmed as described above.

Step 580 states to activate the electrosurgical ablation catheter to ablate the target tissue. After ablation, the catheter is retracted from the patient.

Step 590 states to confirm target tissue ablation. The physician may monitor and confirm ablation of the tumor in real time using the bronchoscope, sensors including electrodes and thermocouples, or other imaging techniques. Ablation duration, tissue temperature, energy delivered, may also be monitored and the procedure may be terminated when a threshold level is attained.

Tumor Outside the Airway—Create Access Channel

With reference again to step 520, in the event the target is determined to be outside of the airway (e.g., in the parenchymal lung tissue), method 500 proceeds to step 522.

Step 522 states to plan the bronchoscopic route to an exit or egress opening along the airway and in the vicinity of the target tissue, and to plan a route extension from the egress opening to the target tissue.

In embodiments, planning an exit or egress opening from the airway and to the target tissue outside of the airway is performed based on a number of constraints. Examples of constraints include, without limitation, proximity to the target tissue, avoiding obstacles such as blood vessels, and physical limitations of the instruments to be used during the procedure such as size, flexibility, and bend constraints. Exemplary techniques to plan the route are descried in U.S. Pat. Nos. 8,709,034 and 9,037,215.

Step 524 states to advance the bronchoscope to a position along the airway in the vicinity of the candidate exit opening.

Step 526 states to create an access pathway to the target tissue. Particularly, step 526 states to create the opening through the airway wall, and tunnel to the tumor to create an access passage along the pre-planned route extension.

In an embodiment, the egress hole is created with a catheter fed through the bronchoscope having a sharp tip. An example of a needle catheter suitable to create the hole is described in U.S. Pat. No. 8,517,955.

In an embodiment, the hole is dilated. Openings may be enlarged using, for example, enlargeable members (e.g., balloon) or fixed tapered dilators.

An elongate tube is advanced through the hole and to the tumor. The tube may be advanced over a wire or needle, or the tube may be navigated to the tumor. In embodiments, the tube includes a removable obturator to prohibit the tube from becoming filled with tissue as the tube is advanced through the tissue.

Once the tube is in position, and the position is confirmed, the intermediate instruments such as an obturator, dilator, guidewire, or needles are retracted leaving an open channel through the tube. Position confirmation, or tracking, of the instruments for accessing the tumor can be performed by a wide range of guidance and location techniques including, without limitation, fluoroscopy or use of electromagnetic sensors. Examples of tracking and guidance techniques are described in U.S. Pat. Nos. 6,380,732 and 9,265,468 and US Patent Publication no. 2016/0180529.

Although a route extension has been described above, various techniques to create and install an access passageway to the tumor are described in the following patent publications including, without limitation, U.S. Pat. Nos. 8,784,400 and 8,709,034. See also, Anciano et al., Going Off Road The First Case Reports of the Use of the Transbronchial Access Tool With Electromagnetic Navigational Bronchoscopy, J Bronchol Intervent Pulmonol, Vol. 24, No. 3, July 2017.

Once the access passageway is installed (such as, e.g., the sheath 302 shown in FIG. 4), the procedure to treat the tumor may be performed as described herein with reference to steps 550-590, except the ablation instruments are advanced to the tumor through the access passageway instead of solely along the airway.

Therapeutic Agent Delivery Via Microspheres

Figure 6:
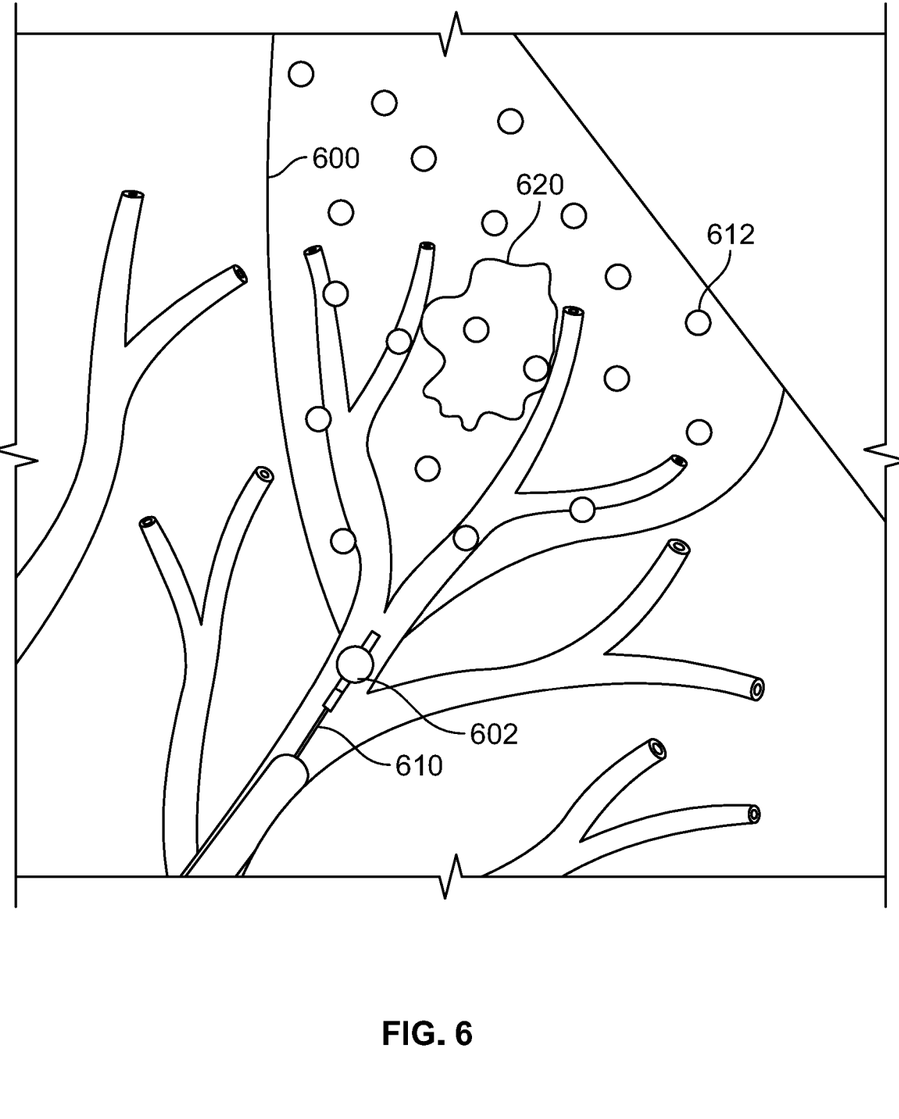
FIG. 6 is an illustration of a method for treating a lung tumor via a plurality of implants in accordance with one embodiment of the invention.

FIG. 6 illustrates ablation of a lung tumor 620 by implanting a plurality of therapeutic agent delivery vehicles 612 in accordance with another embodiment of the invention.

Particularly, a number of particles or microspheres 612 are shown implanted in the vicinity of the tumor 620 and a condensable vapor 600 is delivered from the end of the catheter 610 into the target region.

The microspheres are adapted to temporarily hold and deliver a therapeutic agent to the tumor. The microspheres may be preloaded with the agent, and then implanted in the lung. The position of the microspheres may be detected under imaging such as, for example, radiography or MRI.

The size of the microspheres may vary. In embodiments, the microspheres range from between 0.1 and 1000 µm.

The material of the microspheres may also vary. Exemplary materials of the microspheres include, without limitation, polymer, glass, ceramic. Examples of microspheres are FluoSpheres (manufactured by Thermo Fisher, Eugene, Oreg.).

Examples of therapeutic agents to be delivered by the microspheres include, without limitation, chemotherapy drugs, checkpoint inhibitor, immunotherapy agents, antibiotics or antiseptic agents.

In embodiments, the microspheres release the therapeutic agent over time. In embodiments, the therapeutic agent is heat activated, and treats the tumor.

Optionally, additional energy (e.g., RF ablation) or other treatment and ablation modalities may be applied to the tumor. Preferably, multiple modalities are applied in only one first treatment procedure.

Alternative Embodiments

A wide range of energy modalities may be employed in accordance with the present invention. Examples of suitable energy modalities include RF, laser, microwave, cryogenic fluid, resistive heating, ultrasound and other energy delivery mechanisms for heating a target lung volume.

In another embodiment, a method of treating a suspect tissue mass comprises: delivering a heat activated therapeutic agent to the suspect tissue mass; delivering a condensable vapor comprising water to the suspect tissue mass to activate the heat activated therapeutic agent; and delivering energy to heat the suspect tissue mass to destroy the suspect tissue mass from the inside out.

In embodiments, the heat activated therapeutic agent can be delivered systemically and only activated in the suspect tissue mass where the vapor is delivered.

In embodiments, the heat activated therapeutic agent is delivered via a bronchoscopic aerosol.

The agents delivered in the method may vary widely. Examples of heat activated therapeutic agents include, without limitation, a chemotherapy drug, immunotherapy agent, or a checkpoint inhibitor.

Additionally, it is to be understood that the order of the modalities may vary. In embodiments, the vapor ablation may be performed prior to the second modality or vice versa.

The invention has been discussed in terms of certain embodiments. One of skill in the art, however, will recognize that various modifications may be made without departing from the scope of the invention. For example, numerous variations, changes, and substitutions will now occur to those skilled in the art without departing from the invention. Moreover, while certain features may be shown or discussed in relation to a particular embodiment, such individual features may be used on the various other embodiments of the invention.

The invention claimed is:

1. A method of treating a lung nodule in a lung, the lung nodule comprising a periphery and an interior, the method comprising:
    assessing the periphery of the lung nodule for symmetry, and distributing heat across the periphery of the lung nodule based on assessing the periphery of the lung nodule for symmetry, wherein the step of distributing heat is performed by advancing a catheter along an airway in the lung to a location proximal to a lung region surrounding the lung nodule and delivering a condensable vapor from the catheter into the lung region surrounding the lung nodule such that the lung nodule is engulfed or encapsulated by the condensable vapor; and
    assessing the interior of the lung nodule for increased tissue density for whether to apply a second ablation modality; and
    directly applying heat from a point source to the interior of the lung nodule based on the density of the interior of the lung nodule; and wherein the steps of distributing heat and directly applying heat are performed in a first treatment procedure.

2. The method of claim 1 wherein the step of directly applying heat to the interior of the lung nodule comprises advancing an electrosurgical instrument into direct contact with the lung nodule, and activating the instrument.

3. The method of claim 2 wherein the electrosurgical instrument is an RF energy catheter.

4. The method of claim 1, further comprising delivering a therapeutic agent to the lung nodule.

5. The method of claim 4 wherein the therapeutic agent is selected from the group consisting of an immunotherapy agent, sclerosing agent, and chemotherapy drug.

6. The method of claim 4 wherein the therapeutic agent is an antibiotic or antiseptic agent.

7. The method of claim 4 further comprising implanting microspheres in the vicinity of the lung nodule, and wherein the microspheres comprise the therapeutic agent and the therapeutic agent is released to the lung nodule from the microspheres.

8. The method of claim 7 further comprising detecting the microspheres under imaging.

9. The method of claim 8 wherein the imaging comprises radiography or MRI.

10. The method of claim 1 wherein the condensable vapor is delivered sufficient to fill the lung region, and wherein the lung region is a segment or sub-segment of a lobe of the lung.

11. A method of treating a lung nodule in a lung, the lung nodule comprising a solid mass comprising an exterior and an interior, the method comprising:
   identifying the exterior and interior of the solid mass;
   assessing tissue density of the interior relative to the exterior of the solid mass for increased tissue density;
   heating the lung nodule by a first modality from the whole exterior of the lung nodule inwards if the exterior of the lung nodule is less dense than the interior;
   heating by a second modality different than the first modality the lung nodule from the interior outwards if the interior of the lung nodule is more dense than the interior;
   monitoring a first ablation region and a second ablation region arising from the first modality and second modality of heating, and
   confirming an overlap zone between the first ablation region and second ablation region.

12. The method of claim 11 wherein the heating by the first modality comprises delivering a condensable vapor to the lung nodule.

13. The method of claim 12 wherein the heating by the second modality comprises applying electrosurgical energy to the lung nodule.

14. The method of claim 13 wherein the first modality is performed prior to the second modality.

15. The method of claim 14 wherein the second modality is bronchoscopic radio frequency ablation.

16. The method of claim 11 further comprising assessing the exterior of the lung nodule for non-uniformity prior to the step of heating by the first modality and heating by the first modality based on the assessing the exterior of the lung nodule.

17. The method of claim 11 wherein the second ablation region grows outward.

* * * * *